United States Patent
Karanam et al.

(10) Patent No.: US 11,941,738 B2
(45) Date of Patent: Mar. 26, 2024

(54) SYSTEMS AND METHODS FOR PERSONALIZED PATIENT BODY MODELING

(71) Applicant: Shanghai United Imaging Intelligence Co., Ltd., Shanghai (CN)

(72) Inventors: Srikrishna Karanam, Brighton, MA (US); Meng Zheng, Cambridge, MA (US); Ziyan Wu, Lexington, MA (US)

(73) Assignee: Shanghai United Imaging Intelligence Co., Ltd., Shanghai (CN)

( * ) Notice: Subject to any disclaimer, the term of this patent is extended or adjusted under 35 U.S.C. 154(b) by 63 days.

(21) Appl. No.: 17/513,392

(22) Filed: Oct. 28, 2021

(65) Prior Publication Data
US 2023/0132479 A1    May 4, 2023

(51) Int. Cl.
*G06T 13/40*    (2011.01)
*G06T 17/20*    (2006.01)
*G06T 19/20*    (2011.01)

(52) U.S. Cl.
CPC .............. *G06T 13/40* (2013.01); *G06T 17/20* (2013.01); *G06T 19/20* (2013.01); *G06T 2210/41* (2013.01); *G06T 2219/2004* (2013.01)

(58) Field of Classification Search
CPC ..... G06T 13/40; G06T 17/20; G06T 2210/41; G06T 2219/2004; G06T 19/20
See application file for complete search history.

(56) References Cited

U.S. PATENT DOCUMENTS

| | | | |
|---|---|---|---|
| 10,529,137 B1* | 1/2020 | Black | G06T 15/04 |
| 10,546,417 B2 | 1/2020 | Black et al. | |
| 11,062,476 B1* | 7/2021 | Bigontina | G06V 10/454 |
| 2020/0268251 A1 | 8/2020 | Hao et al. | |
| 2020/0312011 A1* | 10/2020 | Kopeinigg | G06T 19/006 |
| 2021/0019507 A1* | 1/2021 | Brookshire | G06V 10/764 |
| 2021/0232924 A1* | 7/2021 | Sun | G06V 10/82 |

OTHER PUBLICATIONS

Karanam, Srikrishna et al., "Towards Contactless Patient Positioning", IEEE Transactions on Medical Imaging, vol. 39, No. 8, Aug. 2020, 10 pages.

(Continued)

*Primary Examiner* — King Y Poon
*Assistant Examiner* — Vincent Peren
(74) *Attorney, Agent, or Firm* — Zhong Law LLC

(57) ABSTRACT

A three-dimensional (3D) model of a person may be obtained using a pre-trained neural network based on one or more images of the person. Such a model may be subject to estimation bias and/or other types of defects or errors. Described herein are systems, methods, and instrumentalities for refining the 3D model and/or the neural network used to generate the 3D model. The proposed techniques may extract information such as key body locations and/or a body shape from the images and refine the 3D model and/or the neural network using the extracted information. In examples, the 3D model and/or the neural network may be refined by minimizing a difference between the key body locations and/or body shape extracted from the images and corresponding key body locations and/or body shape determined from the 3D model. The refinement may be performed in an iterative and alternating manner.

16 Claims, 8 Drawing Sheets

(56) References Cited

OTHER PUBLICATIONS

Ching, William et al., "Patient-based Radiographic Exposure Factor Selection: A Systematic Review", Journal of Medical Radiation Sciences, vol. 61, No. 3, Sep. 2014, 15 pages.

Kanazawa, Angjoo et al., "End-to-end Recovery of Human Shape and Pose", Conference on Computer Vision and Pattern Recognition, Jun. 2018, 10 pages.

Kolotouros, Nikos et al., "Learning to Reconstruct 3D Human Pose and Shape via Model-fitting in the Loop", International Conference on Computer Vision, Sep. 2019, 10 pages.

Georgakis, Georgios et al., "Hierarchical Kinematic Human Mesh Recovery", European Conference on Computer Vision, Jul. 2020, 17 pages.

Fang, Yicheng et al., "Sensitivity of Chest CT for Covid-19: Comparison to RT-PCR", Radiology, vol. 296, No. 2, Feb. 2020, 3 pages.

Kass, David et al., "Obesity Could Shift Severe COVID-19 Disease to Younger Ages", Lancet, vol. 395, Issue 10236, London, England, May 2020, 2 pages.

Fischer, John, "United Imaging Debuts World's First Ultra-wide 75-cm Bore MR at RSNA", DOTmed, Dec. 2019.

Loper, Matthew et al., "SMPL: A Skinned Multi-Person Linear Model", ACM Transactions on Graphics, vol. 34, Issue 6, Nov. 2015, 16 pages.

Loper, Matthew et al., "MoSh: Motion and Shape Capture from Sparse Markers", ACM Transactions on Graphics, vol. 33, Issue 6, Nov. 2014, 13 pages.

Sam Johnson and Mark Everingham, "Clustered Pose and Nonlinear Appearance Models for Human Pose Estimation", Proceedings of the British Machine Vision Conference, Leeds, UK, Sep. 2010, 11 pages.

Sam Johnson and Mark Everingham, "Learning Effective Human Pose Estimation from Inaccurate Annotation", IEEE Conference on Computer Vision and Pattern Recognition, Jul. 2011, 8 pages.

Andriluka, Mykhaylo et al., "2D Human Pose Estimation: New Benchmark and State of the Art Analysis", 2014 IEEE Conference on Computer Vision and Pattern Recognition, Jun. 2014, 8 pages.

Lin, Tsung-Yi et al., "Microsoft COCO: Common Objects in Context", European Conference on Computer Vision, Lecture Notes in Computer Science, vol. 8693, Feb. 2015, 15 pages.

Ionescu, Catalin et al., "Human3.6M: Large Scale Datasets and Predictive Methods for 3d Human Sensing in Natural Environments", IEEE Transactions on Pattern analysis and Machine Intelligence, vol. 36, No. 7, Jul. 2013, 15 pages.

Bogo, Federica et al., "Keep it SMPL: Automatic Estimation of 3D Human Pose and Shape from a Single Image", European Conference on Computer Vision, Oct. 2016, 18 pages.

Joo, Hanbyul et al., "Exemplar Fine-Tuning for 3D Human Model Fitting Towards In-the-Wild 3D Human Pose Estimation", 2021 International Conference on 3D Vision, London, UK, Oct. 2021, pp. 42-52.

Newell, Alejandro et al., "Stacked Hourglass Networks for Human Pose Estimation", European Conference on Computer Vision, Jul. 2016, 17 pages.

Cao, Zhe et al., "OpenPose: Realtime Multi-person 2D pose Estimation Using Part Affinity Fields", IEEE Transactions on Pattern Analysis and Machine Intelligence, May 2019, 14 pages.

Xiao, Bin et al., "Simple Baselines for Human Pose Estimation and Tracking", European Conference on Computer Vision, Apr. 2018, 16 pages.

Sun, Ke et al., "Deep High-Resolution Representation Learning for Human Pose Estimation", 2019 IEEE/CVF Conference on Computer Vision and Pattern Recognition, Jun. 2019, pp. 5686-5696.

Jin, Sheng et al., "Differentiable Hierarchical Graph Grouping for Multi-Person Pose Estimation", European Conference on Computer Vision, Jul. 2020, pp. 718-734.

Zhang, Feng et al., "Distribution-Aware Coordinate Representation for Human Pose Estimation", 2020 IEEE/CVF Conference on Computer Vision and Pattern Recognition, Sep. 2020, 10 pages.

Sijin Li and Antoni Chan, "3D Human Pose Estimation from Monocular Images with Deep Convolutional Neural Network", Asian Conference on Computer Vision, Nov. 2014, 16 pages.

Tome, Denis et al., "Lifting from the Deep: Convolutional 3D Pose Estimation from a Single Image", The IEEE Conference on Computer Vision and Pattern Recognition, Jul. 2017, 2 pages, "Supplementary Material".

Pavlakos, Georgios et al., "Coarse-to-Fine Volumetric Prediction for Single-Image 3D Human Pose", Conference on Computer Vision and Pattern Recognition, Nov. 2016, 10 pages.

Pavlakos, Georgios et al., "Ordinal Depth Supervision for 3D Human Pose Estimation", 2018 IEEE/CVF Conference on Computer Vision and Pattern Recognition, Jun. 2018, 10 pages.

Martinez, Julieta et al., "A Simple Yet Effective Baseline for 3D Human Pose Estimation", International Conference on Computer Vision, May 2017, 10 pages.

Habibie, Ikhsanul et al., "In the Wild Human Pose Estimation Using Explicit 2D Features and Intermediate 3D Representations", IEEE Conference on Computer Vision and Pattern Recognition, Apr. 2019, 10 pages.

Kun, Zhou et al., "HEMlets Pose: Learning Part-Centric Heatmap Triplets for Accurate 3D Human Pose Estimation", International Conference on Computer Vision, Oct. 2019, 10 pages.

Iqbal, Umar et al., "Weakly-Supervised 3D Human Pose Learning via Multi-View Images in the Wild", 2020 IEEE/CVF Conference on Computer Vision and Pattern Recognition, Jun. 2020, 10 pages.

Zeng, Ailing et al., "SRNet: Improving Generalization in 3D Human Pose Estimation with a Split-and-Recombine Approach", European Conference on Computer Vision, Jul. 2020, 25 pages.

Pavlakos, Georgiosa et al., "Learning to Estimate 3D Human Pose and Shape from a Single Color Image", 2018 IEEE/CVF Conference on Computer Vision and Pattern Recognition, Jun. 2018, 10 pages.

Kolotouros, Nikos et al., "Convolutional Mesh Regression for Single- Image Human Shape Reconstruction", 2019 Conference on Computer Vision and Pattern Recognition, May 2019, 10 pages.

Xiang, Donglai et al., "Monocular Total Capture: Posing Face, Body, and Hands in the Wild", 2019 Conference on Computer Vision and Pattern Recognition, Dec. 2018, 10 pages.

Nikos Kolotouros and Kostas Daniilidis, "TexturePose: Supervising Human Mesh Estimation with texture Consistency", 2019 International Conference on Computer Vision, Oct. 2019, 10 pages.

Gyeongsik Moon and Kyoung Mu Lee, "I2L-MeshNet: Image-to-Lixel Prediction Network for Accurate 3D Human Pose and Mesh Estimation from a Single RGB Image", 2020 European Conference on Computer Vision, Nov. 2020, 23 pages.

Jiang, Wen et al., "Coherent Reconstruction of Multiple Humans from a Single Image", 2020 Conference on Computer Vision and Pattern Recognition, Jun. 2020, 10 pages.

Sengupta, Akash et al., "Synthetic Training for Accurate 3D Human Pose and Shape Estimation in the Wild", 2020 British Machine Vision Conference, Sep. 2020, 13 pages.

Zanfir, Andrei et al., "Weakly Supervised 3D Human Pose and Shape Reconstruction with Normalizing Flows", 2020 Conference on Computer Vision and Pattern Recognition, Aug. 2020, 17 pages.

Kundu, Jogendra Nath et al., "Appearance Consensus Driven Self-Supervised Human Mesh Recovery", 2020 Conference on Computer Vision and Pattern Recognition, Aug. 2020, 25 pages.

Rueegg, Nadine et al., "Chained Representation Cycling: Learning to Estimate 3D Human Pose and Shape by Cycling Between Representations", 2020 Conference on Computer Vision and Pattern Recognition, Jan. 2020, 8 pages.

Zhang, Jason Y. et al., "Perceiving 3D Human-Objects Spatial Arrangements from a Single Image in the Wild", 2020 European Conference on Computer Vision, Jul. 2020, 30 pages.

Arnab, Anurag et al., "Exploiting Temporal Context for 3D Human Pose Estimation in the Wild", 2019 IEEE/CVF Conference on Computer Vision and Pattern Recognition, Jun. 2019, 10 pages.

Kocabas, Muhammed et al., "VIBE: Video Inference for Human Body Pose and Shape Estimation", 2020 IEEE/CVF Conference on Computer Vision and Pattern Recognition, Jun. 2020, 11 pages.

(56) References Cited

OTHER PUBLICATIONS

Moreno-Noguer, Francesc, "3D Pose Estimation from a Single Image via Distance Matrix Regression", 2017 IEEE Conference on Computer Vision and Pattern Recognition, Jul. 2017, 10 pages.
Biswas, Sandika et al., "Lifting 2D Human Pose to 3D: A Weakly Supervised Approach", 2019 International Joint Conference on Neural Networks, Jul. 2019, 10 pages.
Kang, Yangyuxuan et al., "Explicit Residual Descent for 3D Human Pose Estimation from 2D Joint Locations", 2020 British Machine vision Conference, Jul. 2020, 14 pages.
Ching-Hang Chen and Deva Ramanan, "3D Human Pose Estimation = 2D Pose Estimation + Matching", 2017 Conference on Computer Vision and Pattern Recognition, Dec. 2016, 9 pages.
Iqbal, Umar et al., "A Dual-Source Approach for 3D Human Pose Estimation from a Single Image", Computer Vision and Image Understanding 172:37-49, May 2017, 13 pages.
Pons-Moll, Gerard et al., "Posebits for Monocular Human Pose Estimation", 2014 IEEE Conference on Computer Vision and Pattern Recognition, Jun. 2014, 8 pages.
Choi, Hongsuk et al., "Pose2Mesh: Graph Convolutional Network for 3D Human Pose and Mesh Recovery from a 2D Human Pose", 2020 European Conference on Computer Vision, Nov. 2020, 18 pages.
Mehta, Dushyant et al., "Monocular 3D Human Pose Estimation in the Wild Using Improved CNN Supervision", 2017 International Conference on 3D Vision, Oct. 2017, 16 pages.
Mehta, Dushyant et al., "VNect: Real-time 3D Human Pose Estimation with a Single RGB Camera", ACM Transactions on Graphics, vol. 36, Issue. 4, Jul. 2017, 13 pages.

\* cited by examiner

SYSTEMS AND METHODS FOR PERSONALIZED PATIENT BODY MODELING

BACKGROUND

A three-dimensional (3D) model (e.g., mesh) of a patient's body, that realistically reflects the patient's shape and pose, may be used in a variety of medical applications including patient positioning, surgical navigation, unified medical record analysis, etc. For example, with radiation therapy and medical imaging, success of the procedure often hinges upon having the ability to place and maintain a patient in a desirable position so that the procedure can be performed in a precise and accurate manner. Having real time knowledge about an individual patient's physical characteristics such as the patient's body shape and pose in these situations may bring many benefits including, for example, faster and more accurate positioning of the patient in accordance with a scan or treatment protocol, more consistent results, etc. In other example situations such as during a surgical procedure, information about an individual patient's physique may offer insight and guidance for both treatment planning and execution. The information may be utilized, for instance, to locate and navigate around a treatment site of the patient. When visually presented in real time, the information may also provide means for monitoring the state of the patient during the procedure.

SUMMARY 3D human models may be constructed for a patient using pre-trained artificial neural networks and based on images of the patient. These human models, however, may not accurately represent the real pose and/or shape of the patient's body depicted in the images. Described herein are systems, methods, and instrumentalities for generating individualized (e.g., personalized) human body models based on one or more images (e.g., two-dimensional (2D) images) of a person. The systems, methods, and/or instrumentalities may utilize one or more processors that may be configured to obtain a 3D model of a person such as a skinned multi-person linear (SMPL) model of the person, wherein the 3D model may be generated using one or more neural networks based on one or more images of the person and wherein the one or more neural networks may be pre-trained (e.g., using a benchmark training dataset) to generate the 3D model. The one or more processors described herein may be further configured to obtain the one or more images of the person used to generate the 3D model and determine at least one of a first set of key body locations (e.g., anatomical keypoints such as joint locations) of the person or a first body shape of the person based on the one or more images of the person. The one or more processors described herein may then adjust the 3D model of the person based on at least one of the first set of key body locations of the person or the first body shape of the person. For example, the one or more processors may determine at least one of a second set of key body locations of the person or a second body shape of the person based on the 3D model of the person, and adjust the 3D model of the person by minimizing at least one of a difference between the first set of key body locations and the second set of key body locations or a difference between the first body shape of the person and the second body shape of the person. The first set of key body locations of the person and the first body shape of the person may be determined independently from the second set of key body locations of the person or the second body shape of the person.

In examples, the difference between the first plurality of key body locations of the person and the second set of key body locations of the person may comprise a first Euclidean distance and the difference between the first body shape of the person and the second body shape of the person may comprise a second Euclidean distance. In examples, the system or apparatus that comprises the one or more processors may further include at least one visual sensor configured to capture the one or more images of the person described herein. The visual sensor may include, for example, a color sensor, a depth sensor, or an infrared sensor.

In examples, the one or more processors described herein may be further configured to adjust (e.g., refine) the parameters (e.g., weights) of the one or more neural networks based on at least one of the first set of key body locations of the person or the first body shape of the person. For instance, the one or more processors may be configured to adjust (e.g., refine) the parameters of the one or more neural networks and the 3D model of the person in an iterative and/or alternating manner. In examples, the one or more processors described herein may be further configured to output a representation of the adjusted (e.g., refined) 3D model of the person to a receiving device.

BRIEF DESCRIPTION OF THE DRAWINGS

A more detailed understanding of the examples disclosed herein may be had from the following description, given by way of example in conjunction with the accompanying drawings.

DETAILED DESCRIPTION

The present disclosure is illustrated by way of example, and not by way of limitation, in the figures of the accompanying drawings.

Figure 1:
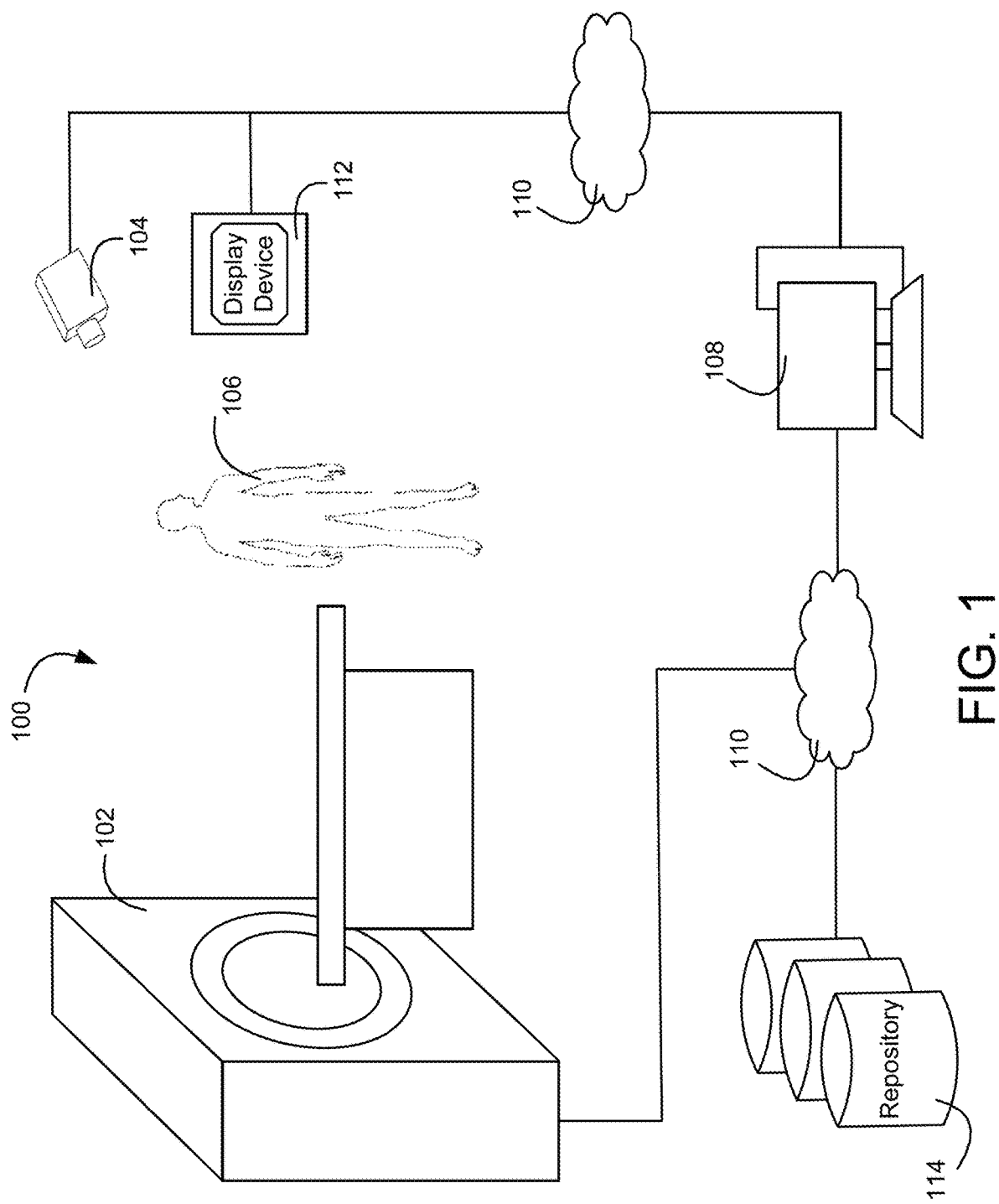
FIG. 1 is a diagram illustrating an example environment in which the systems, methods, and instrumentalities disclosed herein may be applied.

FIG. 1 is a diagram illustrating an example environment 100 in which the methods and instrumentalities disclosed herein may be utilized to adjust an estimated 3D human model. As shown in the figure, the environment 100 may be a scan room configured to provide a medical scan or imaging procedure using a medical scanner 102 (e.g., a computer tomography (CT) scanner, a magnetic resonance imaging (MRI) machine, a positron emission tomography (PET) scanner, an X-ray machine, etc.), even though the environment 100 may also be associated with the performance of other types of medical procedures including, for example, radiation therapy, surgery, etc. (e.g., the environment 100 may be an operating room, a therapy room, and/or the like).

The environment 100 may include at least one sensing device 104 (e.g., an image capturing device) configured to capture images (e.g., 2D or 3D images) of a patient 106, for example, standing in front of the medical scanner 102, lying on a scan or treatment bed, etc. The sensing device 104 may comprise one or more sensors including one or more cameras (e.g., digital cameras, visual sensors, etc.), one or more red, green and blue (RGB) sensors (or other types of visual sensors), one or more depth sensors, one or more RGB plus depth (RGB-D) sensors, one or more thermal sensors such as infrared (FIR) or near-infrared (NIR) sensors, and/or the like. Depending on the type of sensors used, the images captured by the sensing device 104 may include, for example, one or more 2D photos of the patient 106, one or more 2D RGB images of the patient 106, etc. In example implementations, the sensing device 104 may be installed or placed at various distinct locations of the environment 100.

The sensing device 104 may include one or more processors configured to process the images of the patient 106 captured by the sensors described herein. Additionally, or alternatively, the images of the patient 106 captured by the sensing device 104 may be processed by a processing device 108 communicatively coupled to the sensing device 104 and configured to receive the images of the patient 106 captured by the sensing device 104. The processing device 108 may be coupled to the sensing device 104 (e.g., to the sensors comprised in the sensing device 104), for example, via a communication network 110, which may be a wired or wireless communication network. As such, even though the processing unit 108 is shown in FIG. 1 as being located in the same environment 100 as the sensing device 104 and the medical scanner 102, those skilled in the art will understand that the processing unit 108 may also be located away from the environment 100, for example, in a separate room or a different facility.

In response to obtaining (e.g., capturing or receiving) the images of the patient 106, the sensing device 104 and/or the processing device 108 may utilize a neural network to analyze the images (e.g., at a pixel level) and generate a 3D human model for the patient 106 based on the obtained images, wherein the neural network may be pre-trained to generate the 3D human model (e.g., based on a model learned by the neural network through a training process). The 3D human model may include a parametric model such as a skinned multi-person linear (SMPL) model that may indicate the shape (e.g., via a plurality of shape parameters $\beta$), pose (e.g., via a plurality of pose parameters $\theta$), and/or other anatomical characteristics of the patient 106. The 3D human model may be presented, for example, as a 3D mesh.

The sensing device 104 and/or the processing device 108 may be configured to refine the 3D human model generated by the pre-trained neural network based on additional information that the sensing device 104 and/or the processing device 108 may obtain regarding the patient 106. For example, independent from the human model construction process described above, the sensing device 104 and/or the processing device 108 may be configured to extract information regarding the physical characteristics (e.g., key body locations and/or body shape) of the patient 106 from one or more images of the patients 106 captured by the sensing device 104, and use the extracted information to adjust the 3D human model of the patient 106 generated by the neural network. The adjustment may be made, for example, to the shape and/or pose parameters ($\beta$, $\theta$) included in the 3D human model. The images used to perform the adjustment may be, for example, the same images used by the neural network to generate the 3D human model.

In examples, the sensing device 104 and/or the processing device 108 may be further configured to refine the parameters of the neural networks based on the additional information that is used to adjust the 3D human model. For instance, the sensing device 104 and/or the processing device 108 may be configured to refine (e.g., optimize) the parameters of the neural network and the shape and/or pose parameters ($\beta$, $\theta$) of the 3D human model generated by the neural network in an alternating manner based on the additional information. The refinement (e.g., to one or both of the neural network and the 3D human model produced by the neural network) may be performed online (e.g., at an inference time), for example, based on live images of the patient 106 captured by the sensing device 104.

The sensing device 104 and/or the processing device 108 may be configured to display the 3D human model of the patient 106 (e.g., the original 3D model and/or the refined 3D model) on a display device 112. The sensing device 104 and/or the processing device 108 may be further configured to provide (e.g., via the display device 112) a user interface for adjusting the information (e.g., key body locations, shape outlines, etc.) that may be used to refine the 3D human model and/or the neural network. For example, the user interface may be configured to receive user adjustments of key body locations, shape outlines, etc. for refining the 3D human model and/or the neural network. In this way, the sensing device 104 and/or the processing device 108 may protect itself against obvious errors by providing a human (e.g., a clinician) with the ability to adjust/correct values associated with the automatically determined anatomical characteristics of the patient 106. The adjusted/corrected values may then be used to refine/optimize the 3D human model and/or the neural network, as described herein.

The 3D human model generated by the sensing device 104 and/or the processing device 108 may be used to facilitate a plurality of downstream medical applications and services including, for example, patient positioning, medical protocol design, unified or correlated diagnoses and treatments, patient monitoring, surgical navigation, etc. For example, the processing device 108 may determine, based on the 3D human model, whether the position and/or pose of the patient 106 meets the requirements of a predetermined protocol (e.g., while the patient 106 is standing in front of the medical scanner 102 or lying on a scan bed), and provide real-time confirmation or adjustment instructions (e.g., via the display device 112), to help the patient 106 get into the desired position and/or pose. The processing device 108 may also control (e.g., adjust) one or more operating parameters of the medical scanner 102 such as the height of the scan bed based on the body shape of the patient 106 indicated by the 3D human model. As another example, the sensing device 104 and/or the processing device 108 may be coupled with a medical record repository 114 configured to store patient medical records including scan images of the patient 106 obtained through other imaging modalities (e.g., CT, MR, X-ray, SPECT, PET, etc.). The processing device 108 may analyze the medical records of patient 106 stored in the repository 114 using the 3D human model as a reference so as to obtain a comprehensive understanding of the patient's medical conditions. For instance, the processing device 108 may align scan images of the patient 106 from the repository 114 with the 3D human model to allow the scan images to be presented (e.g., via display device 112) and analyzed with reference to the anatomical characteristics (e.g., body shape and/or pose) of the patient 106 as indicated by the 3D human model.

Figure 2:
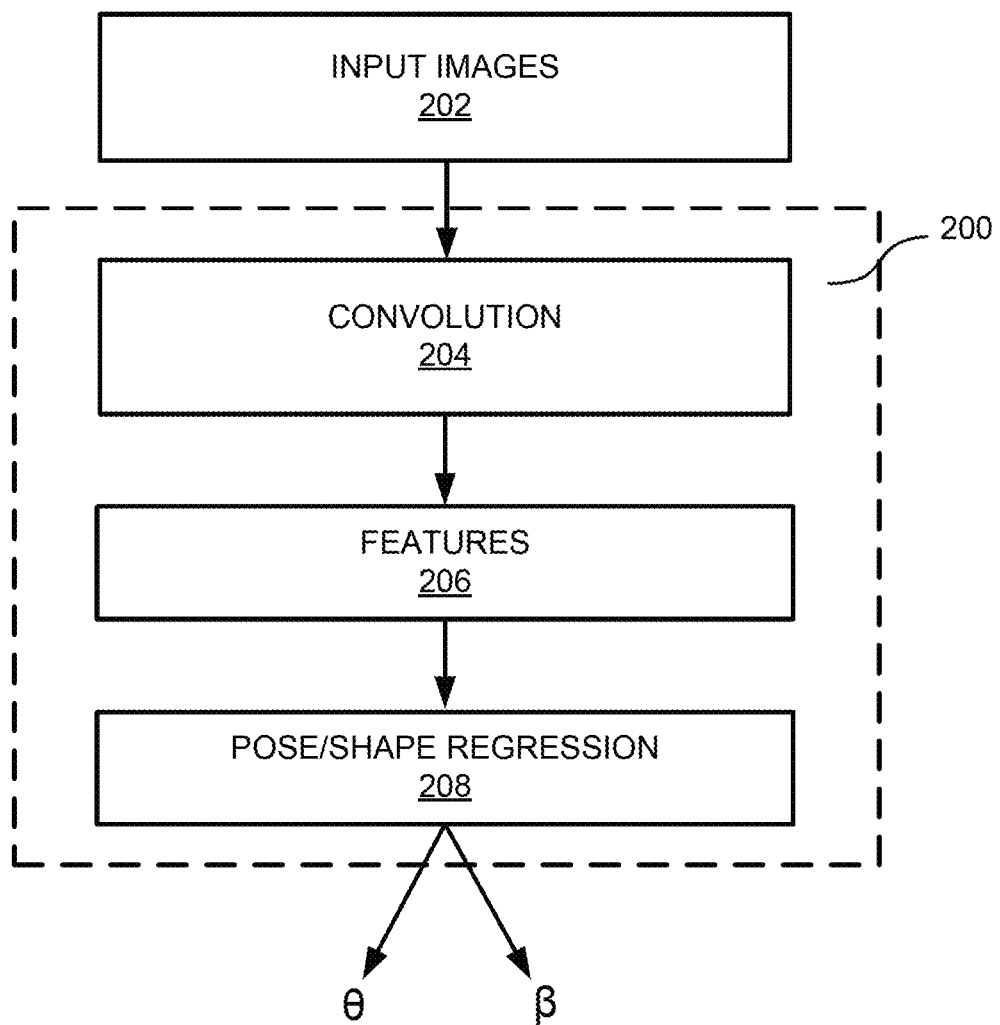
FIG. 2 is a simplified block diagram illustrating an example of a neural network for recovering a 3D human model based on an image.

FIG. 2 illustrates an example of a neural network 200 for recovering (e.g., constructing) a 3D human model based on an image 202 (e.g., a 2D image) of a patient. As shown, given the input image 202 of the patient (e.g., patient 106 of FIG. 1), the neural network may extract features 206 from the image through a series of convolution operations 204, and infer parameters for recovering/estimating the 3D human model by performing regression operations 208 based on the extracted features. The inferred parameters may include pose parameters θ and/or shape parameters β, which may respectively indicate the pose and shape of the patient's body as shown in the image 202.

The neural network 200 may be a convolutional neural network (CNN) comprising multiple layers including, for example, an input layer, one or more convolutional layers, one or more pooling layers, one or more fully connected layers, and/or an output layer. Each of the convolutional layers may include a plurality of filters (e.g., kernels) designed to detect (e.g., extract) the features 206 from the input image 202. The filters may be associated with respective weights that, when applied to an input, produce an output indicating whether a specific feature is detected. The features 206 extracted through the convolution operations may indicate a plurality of key body locations (e.g., anatomical keypoints such as joint locations) of the patient. For example, the features 206 may indicate 23 joint locations of a skeletal rig of the patient as well as a root joint of the patient, which may be used by the neural network 200 to infer 72 pose-related parameters θ (e.g., 3 parameters for each of the 23 joints and 3 parameters for the root joint). The neural network 200 may be also configured to determine the shape parameters β, for example, by conducting a principle component analysis (PCA) of the input image 202 and providing one or more PCA coefficients determined during the process (e.g., the first 10 coefficients of a PCA space) as the shape parameters β.

Using the pose parameters θ and the shape parameters β determined by the neural network 200, the 3D human model of the patient may be constructed, for example, by factorizing the parameters into a shape vector $\beta \in R10$ and a pose vector $\theta \in R72$, and deriving a plurality of vertices (e.g., 6890 vertices) for constructing a representation (e.g., a 3D mesh) of the 3D human model from the shape and pose vectors. Each of these vertices may include respective position, normal, texture, and/or shading information, and the 3D mesh may be generated, for example, by connecting multiple vertices with edges to form a polygon (e.g., such as a triangle), connecting multiple polygons to form a surface, using multiple surfaces to determine a 3D shape, and applying texture and/or shading to the surfaces and/or shapes.

The weights of the neural network 200 may be learned through a training process that may include inputting a large number of images from a training dataset to the neural network (e.g., an instance of the neural network), causing the neural network to make a prediction about the desired 3D human model (e.g., the pose and/or shape parameters associated with the 3D human model), calculating a difference or loss (e.g., based on a loss function such as a mean squared error (MSE) based loss function) between the prediction and a ground truth, and updating the weights of the neural network so as to minimize the difference or loss (e.g., by backpropagating a stochastic gradient descent of the loss through the neural network).

Once trained and given the image 202 of the patient (e.g., at an inference time), the neural network 200 may be capable of estimating the 3D human model described herein. Such an estimated 3D human model, however, may reflect the distribution of the body shapes included in the training dataset (e.g., benchmark datasets) and, as such, may be biased against the patient if the patient's body shape does not conform with the distribution of the training datasets. For example, the distribution of body shapes in a benchmark dataset may reflect the body shape of people having an average weight. As a result, the 3D human model estimated by the neural network 200 may not accurately represent the body shape of the patient if the patient is overweight (e.g., having a larger body size than the average). This phenomenon may be referred to herein as an estimation bias. In addition, the neural network 200 may also encounter other types of prediction errors or defects during an interference process. For example, if a joint of the patient is blocked in the input image 202 (e.g., by another object) or blends with the background of the input image 202 (e.g., due to similarities in color and/or brightness), the neural network 200 may miss the joint in the modeling process and produce a result that is erroneous with respect to either or both of the patient's pose and body shape. Accordingly, post-training refinement of the 3D human model produced by the neural network 200 and/or the neural network 200 itself may be needed.

Figure 3A:
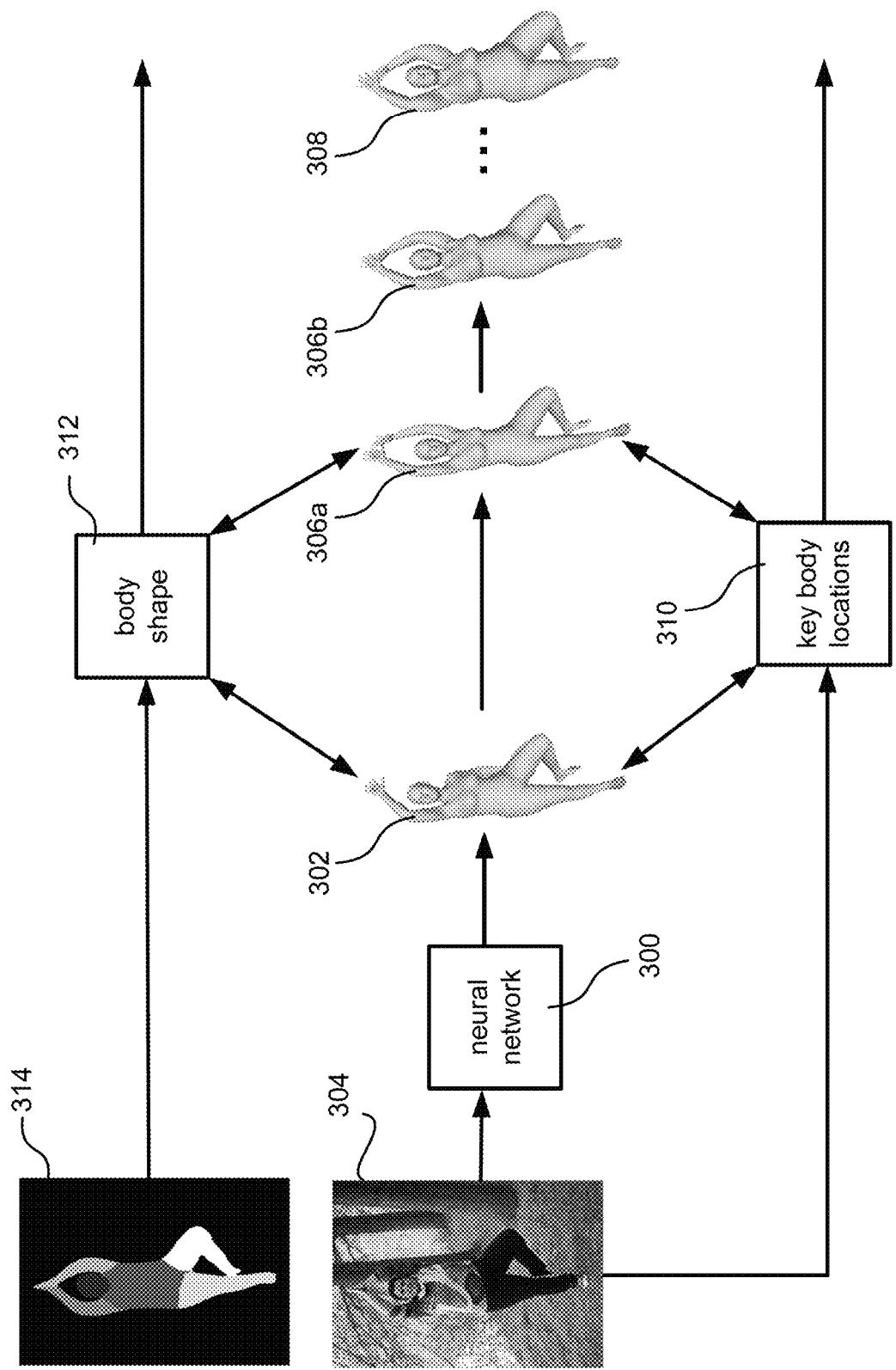
FIG. 3A is a diagram illustrating example techniques for refining a 3D human model predicted by a pre-trained neural network and/or the neural network itself.

FIG. 3A illustrates example techniques for refining a 3D human model 302 (e.g., a 3D mesh) predicted by a neural network 300 (e.g., the neural network 200 shown in FIG. 2) and/or the neural network 300 itself. As discussed herein, the 3D human model 302 may be estimated by the neural network 300 based on an image 304 of a person. Due to issues relating to estimation bias and/or depth ambiguity, however, the 3D human model 302 may not accurately reflect the body shape and/or pose of the person shown in the image 304. For instance, color similarities between the person's left arm and the tree trunk behind the person may cause the 3D human model 302 to incorrectly show that the person's left arm is down rather than up, and estimation bias resulting from the training of the neural network 300 may cause the 3D human model 302 to show a body shape slenderer than the real body shape of the person.

The defects of the 3D human model 302 may be corrected by obtaining additional information regarding the pose and/or shape of the person's body and utilizing the additional information to adjust the pose and/or shape parameters (e.g., θ and/or β of FIG. 2) of the 3D human model 302 so as to construct a refined 3D human model 308. In examples, the refinement may be accomplished through an iterative process during which the original 3D human model 302 may be adjusted gradually (e.g., through one or more intermediate models 306a, 306b, etc.) before the refined 3D human model 306 is obtained. In examples, the additional information used to refine the 3D human model 302 may include key body locations 310 of the person (e.g., anatomical keypoints such as joint locations) determined from the input image 304 and/or body shape information 312 of the person (e.g., a shape outline or shape contour) determined based on a depth image or depth map 314.

The key body locations 310 may be determined independently from the construction of the 3D human model 302. For example, the key body locations 310 may be determined using a different neural network (e.g., a 2D keypoint estimation neural network) than the one (e.g., neural network 300) used to generate the original 3D human model 302. Such a 2D keypoint estimation neural network may be trained using a larger dataset than that used to train neural network 300, for example, since 2D keypoint annotations may be more abundant and/or easier to obtain than 3D annotations. As a result, the independently determined key body locations 310 may more accurately represent the anatomical keypoints of the person depicted in image 304. The body shape information 312 may also be determined independently from the construction of the 3D human model 302. For example, the body shape information 312 may include a shape outline or a shape contour, and the depth map 314 used to determine the shape outline or shape contour may be obtained while the person is in the pose and/or shape shown in image 304 (e.g., the depth map 314 may be obtained simultaneously with image 304 by respective sensing devices 104 shown in FIG. 1). The depth map 314 may include information that indicates respective depth values of the pixels of image 304. Thus, by identifying those pixels that have the same depth value as a body surface pixel of the person, a shape outline or shape contour of the person may be obtained using the depth map 314, even if parts of the person' body are blocked and blend with a background object of image 304 (e.g., since the blocking or blending of certain pixels may not affect the depth values of those pixels).

The key body locations 310 and/or body shape information 312 may be used to guide the adjustment (e.g., optimization) of the pose parameters θ and/or the shape parameters β of the 3D human model 302. For example, in response to obtaining the 3D human model 302, a set of key body locations (e.g., 2D keypoints or key body locations corresponding to the key body locations 310) and/or a shape outline (or contour) may be determined based on the 3D human model 302. The set of key point locations may be determined, for example, based on the vertices comprised in the 3D human models 302 and a mapping relationship between the vertices and 3D key body locations (e.g., the 3D human model 302 may include information indicating which vertices are 3D key body locations). Using the mapping relationship, a plurality of 3D key body locations may be determined based on the vertices of the 3D model 302 and the 3D key body locations may be projected into a 2D image frame (e.g., using predetermined camera and/or projection parameters) to obtain the set of key point locations. Similarly, given the vertices of the 3D human model 302, a shape outline of the person may also be obtained, for example, using the predetermined camera and/or projection parameters.

The set of key body locations and/or shape outline determined based on the 3D human model 302 may then be compared to the independently determined key body locations 310 and/or the shape outline 312, respectively, to determine a difference or loss (e.g., an Euclidean distance) between the two sets of key body locations and/or the two shape outlines. If the loss (e.g., the Euclidean distance) exists (e.g., the loss is greater than a predetermined threshold), an adjustment may be made to the 3D human model 302 (e.g., to the shape parameters β and/or pose parameters θ), for example, based on a gradient descent of the loss, to obtain model 306a. Another set of key body locations and/or shape outline may then be determined based on the adjusted model 306a (e.g., using the techniques described herein), and be compared to the key body locations 310 and/or the shape outline 312, respectively, to determine another difference or loss (e.g., another Euclidean difference) between the two sets of key body locations or two shape outlines. If the loss exists (e.g., the Euclidean distance is greater than a predetermined threshold), a further adjustment may be made to model 306a to obtain another intermediate model 306b, and the operations described above may be repeated until the key body locations and/or shape outline determined from an adjusted model (e.g., the 3D human model 308) align (e.g., substantially align) with the key body locations 310 and/or the shape outline 312. The alignment may be determined to have occurred, for example, if the difference (e.g., an Euclidean distance) between the body locations and/or the shape outlines falls below a predetermined threshold.

Figure 3B:
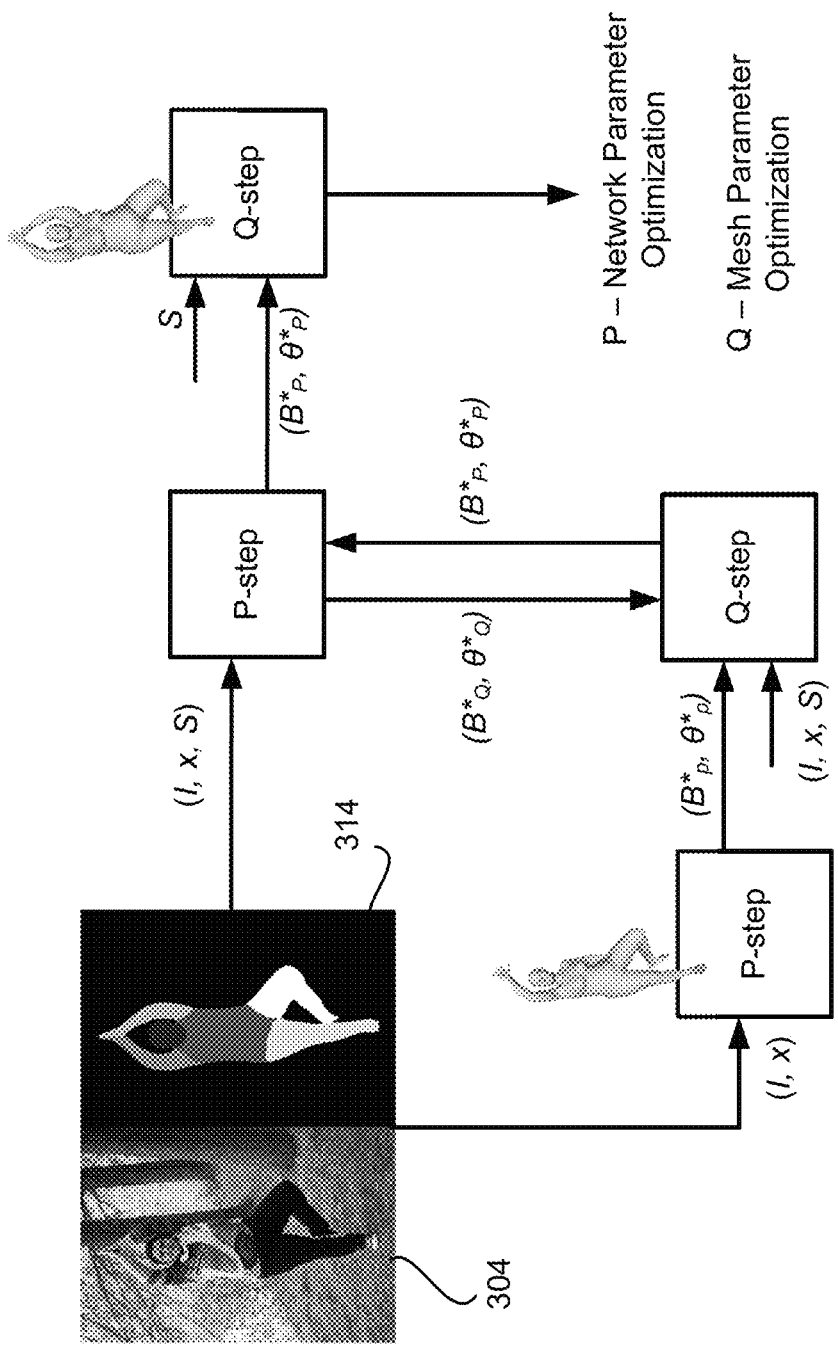
FIG. 3B is a diagram illustrating an example of jointly optimizing a 3D human model and a neural network used to generate the 3D human model.

In addition to adjusting the 3D human model predicted using the pre-trained neural network 300, the neural network 300 itself may also be adjusted (e.g., optimized) based on the additional information (e.g., key body locations and/or shape outline) obtained from the input image 304 and/or the depth map 314. FIG. 3B shows an example of jointly optimizing the parameters Q of a 3D human model (e.g., the 3D model 302 of FIG. 3A) and the parameters P of a neural network (e.g., the neural network 300 of FIG. 3A). The parameters Q may include shape parameters β and/or pose parameters θ of the 3D human model being optimized while the parameters P may include the weights of the neural network being optimized. In examples, the optimization of parameters P and Q may be performed jointly in a multi-step, alternating manner as illustrated by FIG. 3B. For instance, denoting the 3D human model parameters as $\Theta=\{\beta, \theta, s, t\}$ and the neural network parameters as $\Phi$, where β and θ may respectively represent the shape and pose parameters described herein, s may represent one or more scaling parameters s, and t may represent one or more translation parameters, the neural network parameters may be updated (e.g., at the P-step shown in FIG. 3B) based on the following:

$$\alpha^* = \arg_\alpha \min L_{2D}(\pi f(\Phi)(I)), x). \tag{1}$$

where $\alpha^*$ may represent a vector containing updated network parameters $\Phi^*$, I may represent the input image 304, x may represent the key body locations (e.g., joints) predicted based on the image I, $f$ may represent a composition of the functions for mapping the mesh parameters $\Theta$ to vertices V and mapping the vertices V to 3D key body locations (e.g., joints) X, $\pi$ may represent a camera model used to project the 3D key body locations (e.g., joints) to 2D points, and min $L_{2D}$ may represent an effort to minimize a loss function $L_{2D}$ that represents a deviation of the predicted key body locations and a ground truth.

Given $\Phi^*$, the neural network may predict updated values for the mesh parameters $\Theta$ as: $\Theta^*_0 = [\beta^*, \theta^*, s^*, t^*] = \Phi^*(I)$. This $\Theta^*_0$ may then be used as initial parameters to optimize the mesh parameters $\Theta$ (e.g., at the Q-step shown in FIG. 3B) to $\Theta^*_1$, as shown below:

$$\Theta^*_1 = \arg_\Theta \min L_{2D}(\pi M(\beta,\theta),x) + L_\theta(\theta) + L_{shape} \tag{2}$$

where M may represent an SMPL mapping, $L_{shape}$ and $L_\theta(\theta)$ may represent respective loss functions associated with the estimation of shape and/or pose (e.g., based on part-based segmentation labels such as a six-part segmentation strategy including head, torso, left/right arms, and left/right leg), and $\pi$, x, and min $L_{2D}$ may have the same meaning described above.

$\Theta^*_1$ of equation (2) may then be used as an explicit regularization term to further optimize the neural network parameters (e.g., at the P-step shown in FIG. 3B), for example, by modifying equation (2) as follows:

$$\alpha^* = \arg_\alpha \min L_{2D}(\pi f(\Phi(I)), x) + \|\Theta - \Theta^*_1\|_2^2 + L_{shape}. \quad (3)$$

where the various symbols may have the same meaning described here. Given the further adjusted network parameters $\Phi^*$ (e.g., contained in the vector $\alpha^*$), the mesh parameters $\Theta$ may also be further optimized (e.g., at the Q-step shown in FIG. 3B) as $\Theta^*_2 = [\beta^*, \theta^*, s^*, t^*] = \Phi^*(I)$. And the operations described above may be repeated, leading to an iterative alternating optimization of $\Theta$ and $\alpha$, respectively.

The optimization techniques described herein may be used as a drop-in to improve the performance of a pre-trained 3D body estimation neural network (e.g., the neural network 200 of FIG. 2 and 300 of FIG. 3A). Issues associated with overfitting, estimation bias, and/or the like may be resolved so that the results produced by the neural network and/or the neural network itself may be improved to provide accurate fits for different body sizes. As illustrated by FIG. 3B, the optimization techniques may be applied by alternating between the P-steps and Q-steps, leading to improvements in both the human model parameters and the network parameters.

Figure 3C:
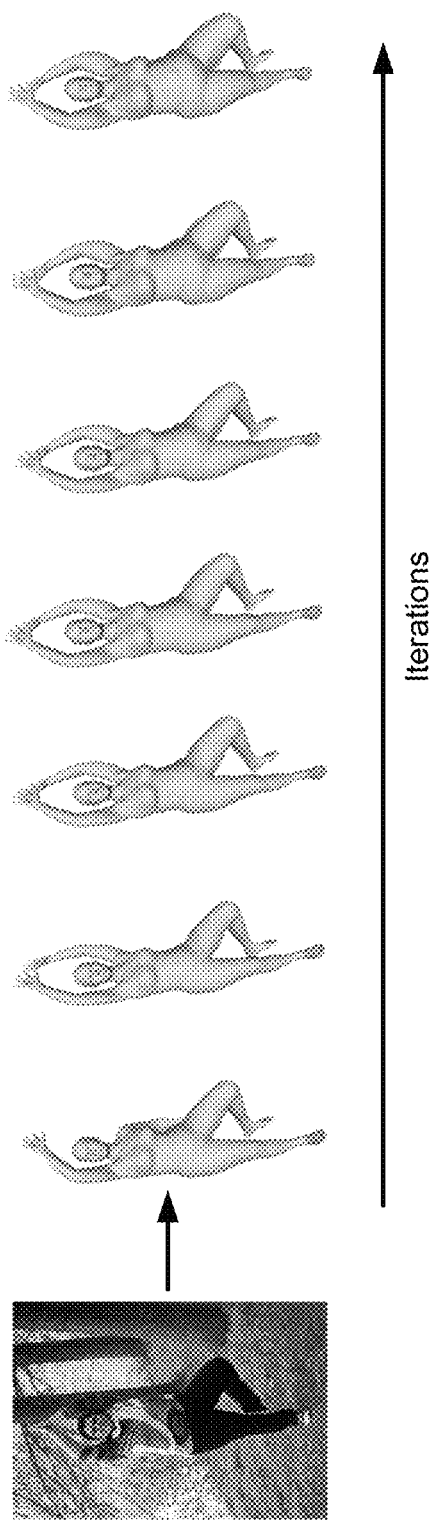
FIG. 3C is a diagram illustrating incremental improvements that may be made to a 3D human model using the techniques described herein.

FIG. 3C illustrates incremental improvements that may be made to a 3D human model using the techniques described with respect to FIG. 3A and FIG. 3B. As shown in FIG. 3C, the 3D human model may become more personalized (e.g., better fit) to the pose and shape of an individual person depicted in an input image 404.

Figure 4:
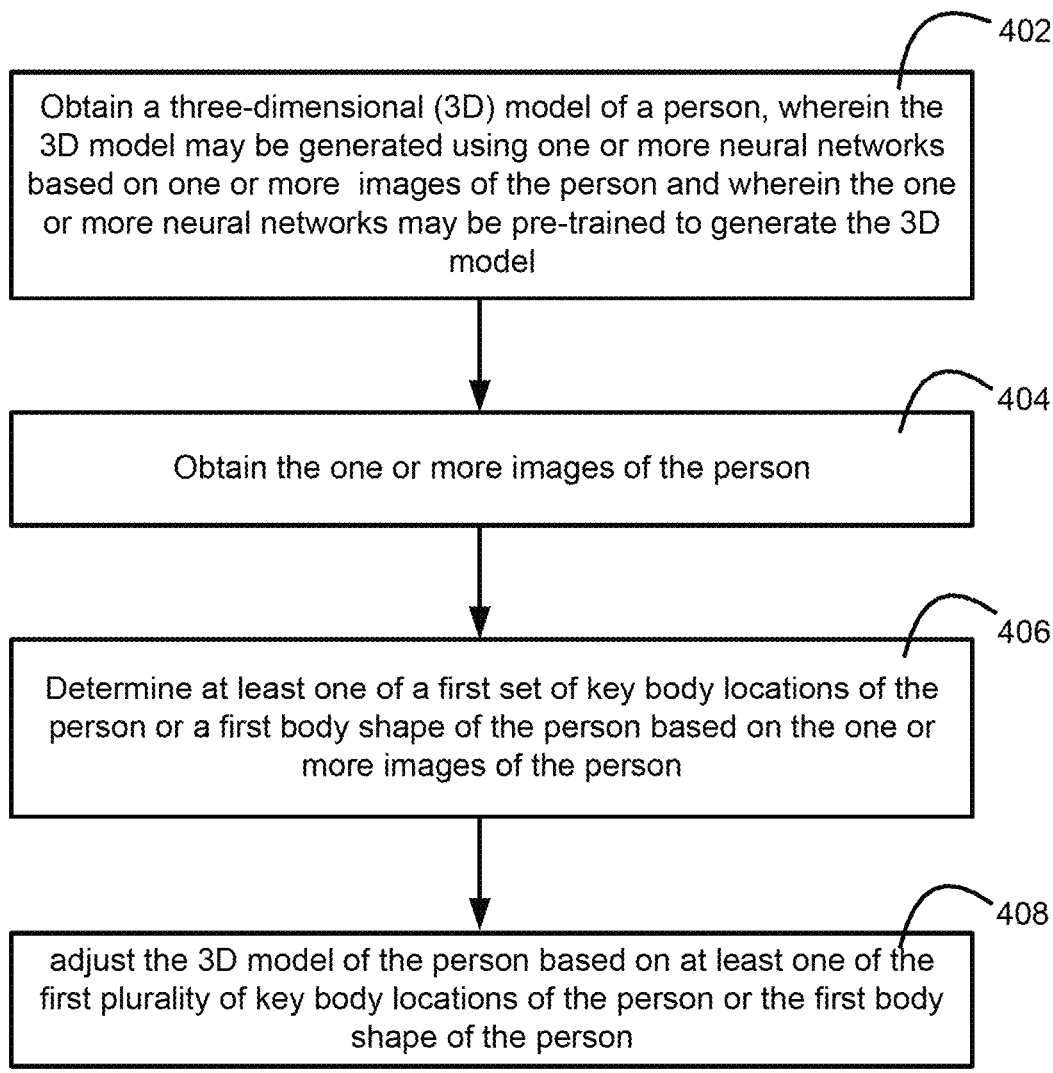
FIG. 4 is a simplified flow diagram illustrating example operations associated with refining a 3D human model based on an image.

FIG. 4 illustrates example operations associated with adjusting a 3D human model based on an image of a person. At 402, a system or apparatus configured to perform the operations may obtain a 3D model of a person, wherein the 3D model may be generated using one or more neural networks based on one or more images (e.g., 2D images) of the person and wherein the one or more neural networks may be pre-trained to generate the 3D model. At 404, the system or apparatus may obtain the one or more images of the person (e.g., 202 of FIG. 2) depicting one or more characteristics (e.g., pose, shape, etc.) of the person. At 406, the system or apparatus may analyze the one or more images of the person to determine at least one of a first set of key body locations of the person or a first body shape of the person based on the images. At 408, the system or apparatus may adjust the 3D model of the person based on at least one of the first set of key body locations of the person or the first body shape of the person as determined at 406. For example, the system or apparatus may compare the first set of key body locations of the person or the first body shape of the person with a second set of key body locations of the person or a second body shape of the person determined based on the 3D model, and adjust the 3D model to minimize the difference between the second sets of key body locations or the two body shapes.

For simplicity of explanation, the operations are depicted and described herein with a specific order. It should be appreciated, however, that these operations may occur in various orders, concurrently, and/or with other operations not presented or described herein. Furthermore, it should be noted that not all operations that the system or apparatus is capable of performing are depicted in FIG. 4 or described herein. It should also be noted that not all illustrated operations may be required to be performed by the system or apparatus.

Figure 5:
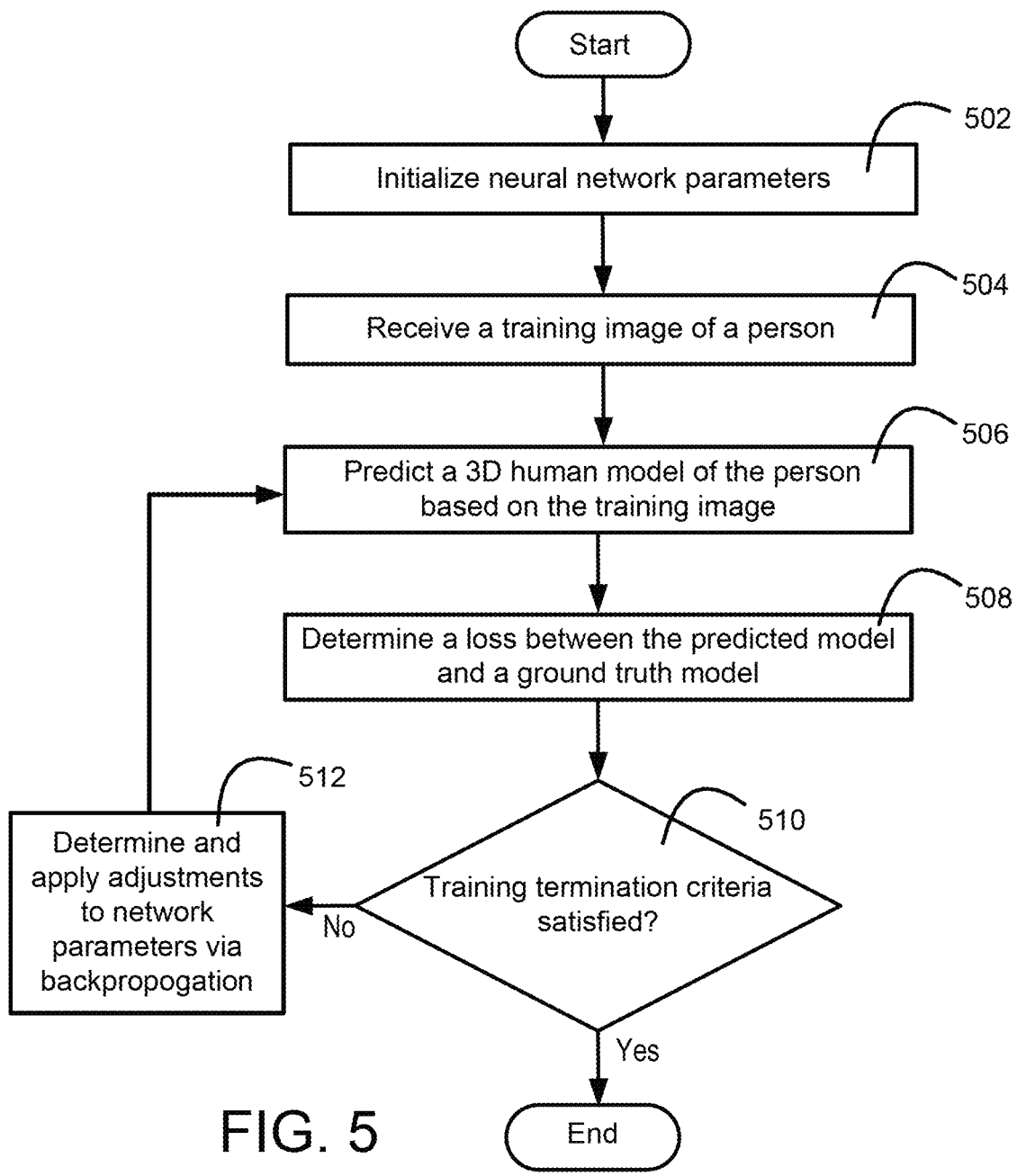
FIG. 5 is a simplified flow diagram illustrating an example method for training a neural network to perform one or more of the tasks described herein.

FIG. 5 illustrates example operations that may be performed while training a neural network (e.g., the neural network 200 of FIG. 2 or 300 of FIG. 3A) in accordance with one or more embodiments described herein. For example, at 502, parameters of the neural network (e.g., weights associated with various filters or kernels of the neural network) may be initialized. The parameters may be initialized, for example, based on samples collected from one or more probability distributions or parameter values of another neural network having a similar architecture. At 504, the neural network may receive a training image of a person (e.g., a 2D image of the person). At 506, the neural network may predict a 3D model based on the training image. At 508, the neural network may compare the predicted model with a ground truth model and determine a loss based on the comparison. The loss may be determined, for example, based on a mean squared error, a L1 normal, a L2 normal, etc. between the predicted model with the ground truth model. At 510, the neural network may determine whether one or more training termination criteria have been satisfied. For example, a training termination criterion may be deemed satisfied if the loss described above is below a predetermined threshold, if a change in the loss between two training iterations (e.g., between consecutive training iterations) is below a predetermined threshold, etc. If the determination at 510 is that a training termination criterion has been satisfied, the training may end. Otherwise, the neural network may at 512 adjust its parameters by backpropagating the loss through the neural network (e.g., based on a gradient descent of the loss), before the training returns to 506.

For simplicity of explanation, the training steps are depicted and described herein with a specific order. It should be appreciated, however, that the training operations may occur in various orders, concurrently, and/or with other operations not presented or described herein. Furthermore, it should be noted that not all operations that may be included in the training process are depicted and described herein, and not all illustrated operations are required to be performed.

Figure 6:
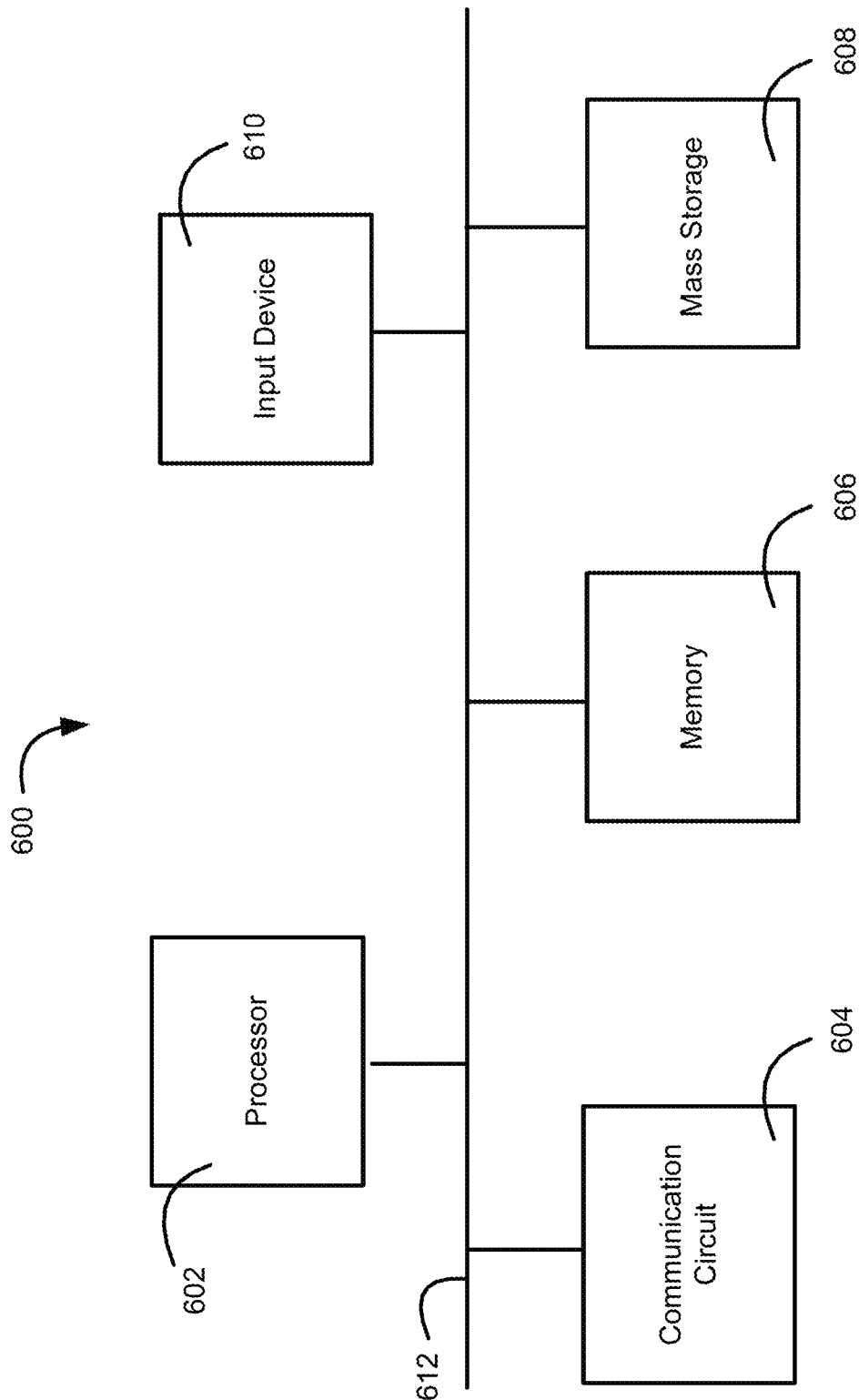
FIG. 6 is a simplified block diagram illustrating an example system or apparatus for performing one or more of the tasks described herein.

The systems, methods, and/or instrumentalities described herein may be implemented using one or more processors, one or more storage devices, and/or other suitable accessory devices such as display devices, communication devices, input/output devices, etc. FIG. 6 is a block diagram illustrating an example apparatus 600 that may be configured to perform the model and neural network optimization tasks described herein. As shown, the apparatus 600 may include a processor (e.g., one or more processors) 602, which may be a central processing unit (CPU), a graphics processing unit (GPU), a microcontroller, a reduced instruction set computer (RISC) processor, application specific integrated circuits (ASICs), an application-specific instruction-set processor (ASIP), a physics processing unit (PPU), a digital signal processor (DSP), a field programmable gate array (FPGA), or any other circuit or processor capable of executing the functions described herein. The apparatus 600 may further include a communication circuit 604, a memory 606, a mass storage device 608, an input device 610, and/or a communication link 612 (e.g., a communication bus) over which the one or more components shown in the figure may exchange information.

The communication circuit 604 may be configured to transmit and receive information utilizing one or more communication protocols (e.g., TCP/IP) and one or more communication networks including a local area network (LAN), a wide area network (WAN), the Internet, a wireless data network (e.g., a Wi-Fi, 3G, 4G/LTE, or 5G network). The memory 606 may include a storage medium (e.g., a non-transitory storage medium) configured to store machine-readable instructions that, when executed, cause the processor 602 to perform one or more of the functions described herein. Examples of the machine-readable medium may include volatile or non-volatile memory including but not limited to semiconductor memory (e.g., electrically programmable read-only memory (EPROM), electrically erasable programmable read-only memory (EEPROM)), flash memory, and/or the like. The mass storage device 808 may include one or more magnetic disks such as one or more internal hard disks, one or more removable disks, one or more magneto-optical disks, one or more CD-ROM or DVD-ROM disks, etc., on which instructions and/or data may be stored to facilitate the operation of the processor 602. The input device 610 may include a keyboard, a mouse, a voice-controlled input device, a touch sensitive input device (e.g., a touch screen), and/or the like for receiving user inputs to the apparatus 600.

It should be noted that the apparatus 600 may operate as a standalone device or may be connected (e.g., networked, or clustered) with other computation devices to perform the functions described herein. And even though only one instance of each component is shown in FIG. 6, a skilled person in the art will understand that the apparatus 600 may include multiple instances of one or more of the components shown in the figure.

While this disclosure has been described in terms of certain embodiments and generally associated methods, alterations and permutations of the embodiments and methods will be apparent to those skilled in the art. Accordingly, the above description of example embodiments does not constrain this disclosure. Other changes, substitutions, and alterations are also possible without departing from the spirit and scope of this disclosure. In addition, unless specifically stated otherwise, discussions utilizing terms such as "analyzing," "determining," "enabling," "identifying," "modifying" or the like, refer to the actions and processes of a computer system, or similar electronic computing device, that manipulates and transforms data represented as physical (e.g., electronic) quantities within the computer system's registers and memories into other data represented as physical quantities within the computer system memories or other such information storage, transmission or display devices.

It is to be understood that the above description is intended to be illustrative, and not restrictive. Many other implementations will be apparent to those of skill in the art upon reading and understanding the above description.

What is claimed is:

1. A method for obtaining a personalized human model, the method comprising:
    obtaining a three-dimensional (3D) model of a person, wherein the 3D model is generated using one or more neural networks based on one or more images of the person and wherein the one or more neural networks are pre-trained to generate the 3D model;
    obtaining the one or more images of the person;
    determining, independently from the 3D model generated using the one or more neural networks, at least one of a first set of key body locations of the person or a first body shape of the person based on the one or more images of the person;
    determining at least one of a second set of key body locations of the person or a second body shape of the person based on the 3D model generated using the one or more neural networks; and
    adjusting the 3D model of the person by minimizing at least one of a first Euclidean distance between the first set of key body locations of the person and the second set of key body locations of the person, or a second Euclidean distance between the first body shape of the person and the second body shape of the person.

2. The method of claim 1, wherein at least one of the first set of key body locations of the person or the first body shape of the person is determined using a different neural network than the one or more neural networks used to generate the 3D model.

3. The method of claim 1, further comprising capturing the one or more images of the person with at least one visual sensor.

4. The method of claim 3, wherein the at least one visual sensor comprises a color sensor, a depth sensor, or an infrared sensor.

5. The method of claim 1, further comprising adjusting parameters of the one or more neural networks based on at least one of the first set of key body locations of the person or the first body shape of the person.

6. The method of claim 5, wherein the parameters of the one or more neural networks and the 3D model of the person are adjusted in an alternating manner.

7. The method of claim 1, wherein the at least one of the first set of key body locations of the person or the first body shape of the person is determined further based on one or more additional images not used by the one or more neural networks to generate the 3D model.

8. The method of claim 7, wherein the one or more additional images include a depth image of the person.

9. An apparatus, comprising:
    one or more processors configured to:
        obtain a three-dimensional (3D) model of a person, wherein the 3D model is generated using one or more neural networks based on one or more images of the person and wherein the one or more neural networks are pre-trained to generate the 3D model;
        obtain the one or more images of the person;
        determine, independently from the 3D model generated using the one or more neural networks, at least one of a first set of key body locations of the person or a first body shape of the person based on the one or more images of the person;
        determine at least one of a second set of key body locations of the person or a second body shape of the person based on the 3D model generated using the one or more neural networks; and
        adjust the 3D model of the person by minimizing at least one of a first Euclidean distance between the first set of key body locations of the person and the second set of key body locations of the person, or a second Euclidean distance between the first body shape of the person and the second body shape of the person.

10. The apparatus of claim 9, wherein the at least one of the first set of key body locations of the person or the first body shape of the person is determined using a different neural network than the one or more neural networks used to generate the 3D model.

11. The apparatus of claim 9, further comprising at least one visual sensor configured to capture the one or more images of the person.

12. The apparatus of claim 11, wherein the at least one visual sensor comprises a color sensor, a depth sensor, or an infrared sensor.

13. The apparatus of claim 9, wherein the one or more processors are further configured to adjust parameters of the one or more neural networks based on at least one of the first set of key body locations of the person or the first body shape of the person.

14. The apparatus of claim 13, wherein the one or more processors are configured to adjust the parameters of the one or more neural networks and the 3D model of the person in an alternating manner.

15. The apparatus of claim 9, wherein the at least one of the first set of key body locations of the person or the first body shape of the person is determined further based on one or more additional images not used by the one or more neural networks to generate the 3D model.

16. The apparatus of claim 15, wherein the one or more additional images include a depth image of the person.

* * * * *